(12) United States Patent
Rosenthal et al.

(10) Patent No.: US 8,021,877 B2
(45) Date of Patent: Sep. 20, 2011

(54) PARTICLE PATTERNING CHIP

(75) Inventors: Adam Rosenthal, Cambridge, MA (US);
Joel Voldman, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 457 days.

(21) Appl. No.: 11/400,801

(22) Filed: Apr. 10, 2006

(65) Prior Publication Data

US 2007/0238089 A1    Oct. 11, 2007

(51) Int. Cl.
*C12N 5/00* (2006.01)

(52) U.S. Cl. ........................................................ 435/325

(58) Field of Classification Search ........................ None
See application file for complete search history.

(56) References Cited

U.S. PATENT DOCUMENTS

| | | | |
|---|---|---|---|
| 6,383,813 B1 | 5/2002 | Baxter et al. | |
| 6,653,124 B1 | 11/2003 | Freeman | |
| 2003/0032048 A1 * | 2/2003 | Kim et al. | 435/6 |
| 2003/0032071 A1 | 2/2003 | Wang et al. | |

OTHER PUBLICATIONS

Rettig et al. (Anal. Chem., 2005, vol. 77, p. 5628-5634).*
Folch et al. (Annu. Rev. Biomed. Eng. 2000, vol. 2, p. 227-256).*
Park et al. (Biotechnol. Prog., 2003, vol. 19, p. 243-253).*

* cited by examiner

*Primary Examiner* — Kade Ariani
(74) *Attorney, Agent, or Firm* — Pearl Cohen Zedek Latzer, LLP; Mark S. Cohen

(57) ABSTRACT

This invention provides devices comprising substrates with wells for the patterning of particles or cells. Such devices are loaded with a suspension of particles or cell, and the entrapped particles or cells are transferred to a second substrate, where patterning of individual particles or cells occurs. Methods of cellular analysis, cell growth studies, surface modification, optical display fabrication and curved surface patterning using devices of this invention are described.

25 Claims, 5 Drawing Sheets

3A  3B

PARTICLE PATTERNING CHIP

GOVERNMENT INTEREST STATEMENT

This invention was made in whole or in part with government support under grant number RR 18878 awarded by the National Institute of Health. The government may have certain rights in the invention.

FIELD OF THE INVENTION

The invention relates to the fields of cells, biotechnology, nanoparticles, patterning and nano-technology, in particular methods and devices to pattern particles in predetermined positions on surfaces.

BACKGROUND OF THE INVENTION

The patterning of particles and cells, their positioning in specific locations on a substrate, is an increasingly important tool in a variety of applications, including the control of a cellular microenvironment. The cellular microenvironment is influenced by several factors—including cell-media, cell-matrix, and cell-cell interactions. Cell patterning can be used to manipulate cell-cell interactions, for example, by varying the contact area between two cell types in co-culture. Cell patterning can also be used to direct cell-matrix interactions, controlling the amount of contact area with the extracellular matrix (ECM) or the type of ECM upon which the cell is found.

Cell patterning has the potential to improve devices such as cell-based biosensors, the use of living cells as sensing elements for applications including toxin detection and defense monitoring. Cells have successfully been interfaced to sensing elements to form cell-based biosensors and recent advances in cell patterning may enable reproducible and readily manufactured biosensor devices, which would answer long felt needs for sensitive assays for biodefense application, for example.

Currently, there are a number of techniques for patterning cells. Microfluidic patterning takes advantage of the laminar flows in microfluidic devices to pattern the cell-culture substrate, cells, or cell-culture media. Other methods use physical barriers to position the cells, using for example, microwells or removable elastomeric stencils. Microcontact stamping of matrix proteins patterned onto a substrate and electroactive substrates with an applied voltage to switch the surface properties of the substrate, are both means used to facilitate selective cell attachment to specific regions of a substrate. Electromagnetic forces and optical tweezers have also been used to pattern cells.

To date, these techniques however, suffer limitations in their application in high-throughput settings, lack of resolution at a single cell level, produce unnatural and even traumatic effects on the manipulated cells, and lack the flexibility of manipulating the cells over time in an appropriate cellular milieu.

SUMMARY OF THE INVENTION

In one embodiment, this invention provides a particle patterning device comprising a first substrate and wells, wherein:
   a. said wells are sized so as to accommodate individual particles;
   b. said wells are positioned on or as a part of said substrate; and
   c. said wells are spaced at defined increments of from about 50 µm to about 50 mm between each well in said device.

In one embodiment, the device further comprises second substrate, the long axis of which is positioned approximately parallel to said first substrate, at a distance of between 50 µm-100 mm from said first substrate In one embodiment, the device further comprises a spacer, which is used to position the second substrate at a specified distance from the first substrate, and in one embodiment, the spacer has a height ranging from about 50 µm-100 mm and a width ranging from about 10 µm-1 mm. In one embodiment, the second substrate is coated with a material, which promotes particle adhesion thereto, which, in one embodiment comprises extracellular matrix components, antibodies specific for cell surface molecules, or a combination thereof. In one embodiment, the second substrate is a 96-well plate.

In one embodiment, the first substrate, wells, or a combination thereof is coated with a material, which minimizes particle adhesion thereto, which in one embodiment is teflon, or in another embodiments, is a protein solution, which in one embodiment, comprises Bovine Serum Albumin (BSA).

In one embodiment the first substrate, wells, second substrate or a combination thereof comprise an organic material, or in another embodiment, an inorganic material. In one embodiment the first substrate, wells, second substrate or a combination thereof comprise a semiconducting material, a metal or metal alloy, a transparent material or a metal coated with an organic monolayer or multilayer. In another embodiment, the first substrate, wells, second substrate or a combination thereof comprises a PolyDiMethylSiloxane (PDMS), Si, SiO2, Si covered by SiO2, Glass or TiO2.

In one embodiment, the wells of the device are of equal size, or in another embodiment, of non-equal size. In one embodiment, the wells of the device are circular, square, triangular, rectangular, or any combination thereof, in shape. In one embodiment, the wells of the device are of non-uniform shape. In one embodiment, the wells of the device have a depth of from about 1 nm to about 10 millimeter. In one embodiment, the wells are equally spaced on the substrate, or in another embodiment, the wells are not equally spaced on the substrate.

In one embodiment, the particles have a diameter of about 1-1000 micron, or in another embodiment, the particles have a diameter of about 1-1000 nanometer.

In one embodiment, the device further comprises electrical contacts, ports for the application of fluids, a vacuum or a combination thereof.

In another embodiment, the device further comprises an apparatus for controlling atmospheric conditions in the device.

In another embodiment, the invention provides a flow chamber comprising the device.

In another embodiment, this invention provides a method of particle patterning comprising the steps of:
   a. loading particles on a particle patterning device comprising a first substrate and wells, wherein:
      i. said wells are sized so as to accommodate a requisite number of particles;
      ii. said wells are positioned on or as a part of said substrate; and
      iii. said wells are spaced at defined increments of from about 50 µm to about 50 mm between each well in said device;
   b. ensuring said requisite number of particles are within the wells of said device; and
   c. positioning said device such that its posterior surface is located apically with respect to a second substrate, its long axis is approximately parallel to the long axis of said second substrate and said second substrate is at a specified distance from said device;

whereby said particles are thereby deposited on said second substrate and patterned according to said defined increments.

In one embodiment, the particles are cells, which in some embodiments, vary in terms of type, dimension, experimental manipulation or combination thereof. In some embodiments, the wells comprise individual cells. In some embodiments, the method further comprises the step of assaying the particle or cell.

In another embodiment, this invention provides a method of patterned cell analysis comprising the steps of:
  a. loading cells on a cell patterning device comprising a first substrate and wells, wherein:
    said wells are sized so as to accommodate a requisite number of cells;
    said wells are positioned on or as a part of said substrate; and
    said wells are spaced at defined increments of from about 50 μm to about 50 mm between each well in said device;
  b. ensuring said requisite number of cells are within the wells of said device;
  c. positioning said device such that its posterior surface is located apically with respect to a second substrate, its long axis is approximately parallel to the long axis of said second substrate and said second substrate is at a specified distance from said device, whereby said cells are thereby deposited on said second substrate and patterned according to said defined increments; and
  d. analyzing said patterned cells.

In one embodiment, the analyzing is conducted subsequent to cells spreading, proliferation, assay, or a combination thereof. In one embodiment, the assay is a diagnostic assay.

In one embodiment, the cells are engineered to express at least one desired molecule, or in another embodiment, the cells are contacted with a library of molecules prior to loading of the cells. In one embodiment, the cells are assayed to determine efficacy of a molecule within said library, which in one embodiment, is a drug. In one embodiment, the cells are stem or progenitor cells, and in one embodiment, the cells are engineered to express at least one desired protein. In one embodiment, the cells are cultured under conditions promoting expression of the protein, and in one embodiment, the conditions promote tissue engineering as a function of expression.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 1a depicts a particle patterning device according to embodiments of the invention; FIG. 1b depicts an array of wells of the first substrate in a cell patterning device; FIG. 1c depicts one well of the first substrate in a cell patterning device.

DETAILED DESCRIPTION OF THE INVENTION

Figure 1:
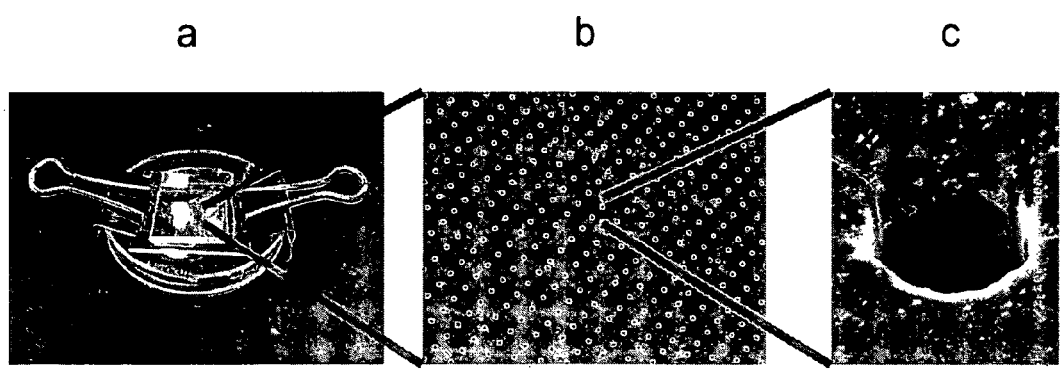
FIG. 1 depicts one embodiment of a cell patterning device.

This invention provides, in one embodiment, a particle patterning device for patterning of micron-scale materials, such as particles and cells.

In one embodiment, this invention provides a particle patterning device comprising a first substrate and wells, wherein:
  a. said wells are sized so as to accommodate individual particles;
  b. said wells are positioned on or as a part of said substrate; and
  c. said wells are spaced at defined increments of from about 50 μm to about 50 mm between each well in said device.

In one embodiment, the term patterning device refers to a device which when utilized, enables the specific deposition of at least one desired material, such as, in some embodiments, particles, or cells, at a desired location, on a substrate.

In one embodiment, the device comprises a first substrate, having wells. In one embodiment, the term "wells" refers to any bounded region of space which can physically accommodate, in whole or in part, a material which is to be patterned. In one embodiment, such a well is not to be constrained by shape or size, which will be a function of the desired application, or material to be deposited. For example, and in one embodiment, should patterning of lymphocytes onto a substrate be desired, then wells for use in a device to effect the same may be roughly circular, and have a diameter of roughly 10 μm, whereas patterning of for example cuboidal cells, such as cells comprising exocrine ducts, etc., may make use of wells which are approximately square in shape, and having a diameter of roughly 40 μm. If patterning of a number of cells is desired, the diameter of the wells may be enlarged so as to accommodate the number of cells.

In one embodiment, the wells have a diameter such that they will accommodate particles, cells or other materials of about 1-1000 micrometer, or in another embodiment, the wells have a diameter such that they will accommodate particles, cells or other materials of about 1-1000 nanometer.

In one embodiment, the wells of the device may be of equal size, or in another embodiment, of non-equal size. In one embodiment, the wells of the device are circular, square, triangular, rectangular, or any combination thereof, in shape. In one embodiment, the wells of the device are of non-uniform shape. In one embodiment, the wells have a tapered shape, such that the apical surface diameter may be larger than a diameter within the well more basally located. In one embodiment, the wells are so constructed, such that a more apically located segment of the well may be readily removed, and a well with an opening with a larger diameter remains.

In one embodiment, one application of such a device comprising tapered wells is to load cells into wells wherein the diameter of the wells ensures that only single cells are loaded. According to this aspect of the invention, and in one embodiment, the apical segment is removed, for example, the well is scored so as to readily allow removal of the segment, and a well with a larger diameter comprising individual cells remains. The cells, according to this embodiment, are then patterned onto a substrate, for example, onto 24-well tissue culture plates, providing a larger area for example, for studies of cell replication rates, arising from a single cell.

In one embodiment, the wells of the device have a depth, which is suitable for the particular application of use of the device. In one embodiment, in devices used for the patterning of cells, the wells will be so constructed so as to have a depth, which accommodates the cells, media and room for gas exchange. In one embodiment, the depth of the wells will be so constructed so as to have an up to 35% excess in height, or in another embodiment, the depth of the wells will be so constructed so as to have an up to 50% excess in height, or in another embodiment, the depth of the wells will be so constructed so as to have an up to 75% excess in height, or in another embodiment, the depth of the wells will be so constructed so as to have an up to 100% excess in height from that of the height of the applied material, cell or particle. In one embodiment, the depth of the wells will comprise up to 20% excess height, or, in another embodiment, up to 10% excess height, or, in another embodiment, up to 5% excess height. In one embodiment, the well height will range from about 1 nm to about 10 millimeter.

In one embodiment, the wells are equally spaced on the substrate, or in another embodiment, the wells are not equally spaced on the substrate.

In one embodiment, the size of the spacing between each well of the devices of this invention and their use, will be a function of the desired application. Such spacing is not to be constrained in any way, and will, in some embodiments, be a function of the substrate onto which the particles or cells or other material is to be deposited, or in other embodiments, be a function of the cells deposited, or in other embodiments, be a function of the type of assay or analysis to be conducted on the patterned particles, cells, etc.

In some embodiments, spacing of the wells will accommodate subsequent transfer of the cells to an industry standard microtiter plate such as, for example, a 24-, 96-, 384-, 768-, or a 1536-well microtiter plate. According to this aspect of the invention, and in one embodiment, the wells comprise a removable apical region, as described herein, which serve to deposit single cells within each well of the device, whose more basal segment, following removal of the removable section, parallels that of the industry standard microtiter plate, and spaced accordingly. In another embodiment, according to this aspect, wells comprise a relatively constant height, however, the individual wells are spaced sufficiently apart such that their inversion onto the industry standard microtiter plate results in single cell deposition within each well of the plate.

In some embodiments, spacing of the wells is at defined increments of from about 50 µm to about 50 mm between each well in said device. In some embodiments, spacing of the wells is at defined increments of from about 10 µm to about 50 µm between each well in said device. In some embodiments, spacing of the wells is at defined increments of from about 50 µm to about 1 mm between each well in said device. In some embodiments, spacing of the wells is at defined increments of from about 1 mm to about 10 mm between each well in said device. In some embodiments, spacing of the wells is at defined increments of from about 50 mm to about 200 mm between each well in said device.

In one embodiment, the term "substrate" refers to the material of which the wells and spacing between them are comprised. In one embodiment, the wells are positioned and/or fixed on a substrate. In one embodiment, the wells are contiguous with the substrate, i.e., the substrate material forms the wells and spaces between them. In one embodiment, the wells communicate between a first outer surface and a second outer surface of the substrate.

In one embodiment, the first substrate, wells, or a combination thereof is coated with a material, which minimizes particle adhesion thereto, which in one embodiment is polytetrafluoroethylene (TEFLON), or in another embodiments, is a protein solution, which in one embodiment, comprises Bovine Serum Albumin (BSA).

In another embodiment, the first substrate may be coated, by microstamping molecules such as polyethylene glycol (PEG) or octadecyl-trichlorosilane (OTS), both of which resist protein adhesion and thereby prevent cell adhesion.

In one embodiment, cells, particles or other materials are applied to the devices of this invention by any means known in the art. For example, cells, particles or other materials may be delivered by directly pipetting them onto the surface of the device either manually or by robotic liquid handling systems. In some embodiments, application is via bulk delivering the cells, particles or other materials in fluid to the surface of the device and removing excess fluid by pipetting, or in some embodiments, via the application of a vacuum, or in some embodiments via the use of a physical implement to remove the cells, such as, for example, a cell scraper or rubber policman. In some embodiments, the cells, particles or other materials are applied via the use of a delivery device with microfluidic channels to deliver the cells to the surface of the device.

In one embodiment, the device further comprises second substrate, the long axis of which is positioned approximately parallel to said first substrate, at a distance of between 50 µm-100 mm from said first substrate.

In one embodiment, the device further comprises a spacer, which is used to position the second substrate at a specified distance from the first substrate, and in one embodiment, the spacer has a height ranging from about 50 µm-100 mm and a width ranging from about 10 µm-1 mm.

In one embodiment, the spacer may be constructed of any material, and may comprise, in some embodiments, materials which prevent or diminish adherence thereto, as described herein.

In one embodiment, the distance between the wells and the second substrate is a function of the spacer. In some embodiments, the spacer is of a width on the scale of a few microns, or a few nanometers to about a few millimeters. In one embodiment, the width of the spacer is dependent on the shape of the enclosed chamber. In one embodiment, the shape of the spacer approximates the shape of the well. In one embodiment, the spacer is constructed to be positioned around a single well, or in another embodiment, a grouping of wells, or in another embodiment, a large array of wells. In some embodiments, the spacer geometry is a reflection of the geometries of the well or wells thus bounded. For example, a square shaped well may have, in some embodiments, a square shaped spacer used. In some embodiments, the spacer is not contiguous, for example, a square shaped spacer, may have a region of one or more of the sides removed. In some embodiments, the spacer may have subcompartments to divide the patterned cells into separate chambers.

In one embodiment, the second substrate is coated with a material, which promotes particle adhesion thereto, which, in one embodiment comprises extracellular matrix components, antibodies specific for cell surface molecules, or a combination thereof. In one embodiment, the second substrate is a 96-well plate.

In one embodiment, the second substrate is comprised of a cellular or particle adherence promoting material. In some embodiments, suitable adherence promoting materials may include, but are not limited to, various carbon coatings, nitrides, metal coatings, metal alloys, biological polymers, glasses, oxides, phosphates and carbides or combinations thereof. In another embodiment, additional materials can be used for coating the substrate to promote adherence, such as, for example, coating or application of cytokines, chemokines, matrix proteins, adhesion molecules, lectins, immunoglobulins, RGD peptides (R: arginine; G: glycine; D: aspartic acid) and others, as will be appreciated by one skilled in the art.

In another embodiment, the adherence promoting materials may include, but are not limited to, an antigen, hapten, enzyme, an enzyme cofactor, a receptor agonist, a carbohydrate, a receptor, and others.

In another embodiment, the adherence promoting materials may include, but are not limited to, an antibody specific for various or specific mammalian cells. For example, anti-Ig kappa light chain antibody, anti-CD45R antibody, or anti-syndecan, may be used to differentially bind B-cells. Antibodies to cytokeratins may differentially bind epithelial cells, etc. Any of the methods known in the art for conjugating an antibody to a solid phase support, can be used in the present invention.

In one embodiment the first substrate, wells, second substrate or a combination thereof comprise an organic material, or in another embodiment, an inorganic material. In one embodiment the first substrate, wells, second substrate or a combination thereof comprise a semiconducting material, a metal or metal alloy, a transparent material or a metal coated with an organic monolayer or multilayer. In another embodiment, the first substrate, wells, second substrate or a combination thereof comprises a PolyDiMethylSiloxane (PDMS), Si, SiO2, Si covered by SiO2, Glass or TiO2.

In one embodiment the first substrate, wells, second substrate or a combination thereof comprise rigid or flexible machinable material such as glass, co-polymer or polymer, for example, urethane, rubber, molded plastic, polymethyl methacrylate (PMMU), polycarbonate, polyvinyl chloride (PVC), polysulfone, and the like.

In one embodiment the first substrate, wells, second substrate or a combination thereof comprise two or more materials, which in one embodiment, are used in a parallel, or in another embodiment, are used in a serial fashion. In one embodiment, the first substrate, wells, second substrate or a combination thereof are hard, or in another embodiment, are flexible. In another embodiment, the first substrate, wells, second substrate or a combination thereof are comprised of a flexible material which can be wrapped around a curved surface.

In one embodiment, the surface is an organic material. In one embodiment the surface is inorganic material. In one embodiment the surface is glass. In one embodiment the surface is Si. In one embodiment the surface is metal. In one embodiment the surface is an inorganic material coated with metal. In one embodiment the surface is an inorganic material coated by an organic material. In one embodiment the surface is transparent. In one embodiment the surface has a cylindrical shape.

In one embodiment, the wells are shaped and sized to hold individual cells such as adherent cells, neoplastic cells, pre-neoplastic cells, neuronal cells, microglia cells, giant cells, hormone secreting cells, metabolism and storage cells, barrier function cells, ECM secreting cells, contractile cells, blood and immune system cell, germ cells, stem cells, fused cells, primary cells, cell lines, bacterial cells, yeast, protests, or any desired cell which can be contained within the device.

In some embodiments, the devices of this invention comprise chips with discrete wells.

In one embodiment, the devices of this invention are formed using the technology of micro- or nano-fabrication. Microfabrication technology, or microtechnology or MEMS, in one embodiment, applies the tools and processes of semiconductor fabrication to the formation of, for example, physical structures. Similarly, nanofabrication technology enables the formation of nanometer scale materials.

Microfabrication technology allows one, in one embodiment, to precisely design features (e.g., wells, channels) with dimensions in the range of <1 mm to several centimeters on chips made of silicon, glass, or plastics, which is scaled down, as will be appreciated by one skilled in the art for the creation of nanometer-sized materials.

In one embodiment, the device of this invention uses biologically applied microtechnology for the creation of large cell patterning arrays that hold and ultimately pattern single-cells when flipped onto a second substrate.

In one embodiment, such chips may be made by pouring a silicone liquid over a master Si wafer with the defining features. The silicone hardens after a few hours and is peeled off. Each silicone sheet can produce 10+ chips, depending on the size of the chips. The master Si wafer is fabricated using photolithography, e-beam lithography, shadow mask lithography, NanoSphere Lithography (NSL), block copolymer lithography and several wafers can be made in a few hours. The master wafers last indefinitely, allowing for the generation of many rounds of chips.

In some embodiments, the devices of this invention may be fabricated by any means known in the art, such as, for example, by modified electroplating (Florio S. M 1997; Otsuka K. 1997), electroforming (Andrea L. E. 1997), electro-etching (Brophy D. J. 1997), with or without lithography. In one embodiment, the device may be prepared by chemical etching.

In some embodiments, the devices of this invention are fabricated using well known molding techniques, such as injection molding, embossing or stamping, or by polymerizing the polymeric precursor material within a mold. Standard soft lithography techniques may also be used to fabricate the devices (see e.g., Love, et al., MRS BULLETIN, pp. 523-527 (July 2001) Delamarche et al,: JOURNAL OF AMERICAN CHEMICAL SOCIETY, Vol. 120, pp. 500-508 (1998), Delamarche et al,: SCIENCE, Vol. 276, pp. 779-781 (May 1997), Quake et al., SCIENCE, Vol. 290, pp. 1536-1540 (Nov. 24, 2000), U.S. Pat. No. 6,090,251, all of which are hereby incorporated by reference).

In some embodiments, the range and height of the wells are defined by the molding technique used. In one embodiment, a master mold is prepared using photoresist and wells ranging from about 1-500 micron in height may be prepared, which dimensions can be expanded, in other embodiments, and will be a function of the material used to mold the wells or the substrate comprising the same. In another embodiment, well diameter can be defined by the photo mask, which can produce diameters of about 1 micron to up to about 100 mm.

In another embodiment, well spacing may also be defined by the photomask. In one embodiment, wells can be constructed so as to be packed as closely together as possible, with sufficient space therebetween to prevent overlap, for example, construction of a 20 micron diameter well, may be accompanied by spacing of the wells on the substrate by about 25 micron. In some embodiments, spacing may be very far apart, and several orders of magnitude larger than the well diameter. It is to be understood that none of the dimensions of the wells, their spacing, height, etc. are to be construed as being restricted in any way, and will vary as a function of the desired application of the particular device.

In one embodiment, the array size may be any to suit a particular application, for example, a 20×20 mm chip may be produced, 50×50 mm, or in other embodiments, larger or smaller chips, and well spacing will be a function of a desired application, and be reflected in the array size, as well.

In one embodiment, the devices of this invention may comprise multiple ports, for the introduction of fluids, the application of a vacuum, or others, as will be appreciated by one skilled in the art. In one embodiment, the device is fabricated in a modular design, such that transport of the device comprising cells, flipping of the first substrate in order to pattern the particles, cells or other materials, and their assay is more readily accomplished. In one embodiment, the device may modularly fit into a holder, which has a height and depth that exceeds that of the device, yet situates the device within. In some embodiments, the modular design of the device enables the robotization of the patterning methods of this invention.

In one embodiment, the device further comprises electrical contacts, ports for the application of fluids, a vacuum or a combination thereof.

In another embodiment, the device further comprises an apparatus for controlling atmospheric conditions in the device.

In one embodiment, the devices of this invention comprise control systems and user interfaces. In one embodiment, control systems comprise on-chip environmental control, or embedded environmental control of the second substrate, or environmental control hookup to the second substrate, to enable multi-hour observation of cells, electronic and fluidic control to automate the sorting process as well as the delivery of reagents to the devices, automated microscopy to perform observation and data acquisition, or a combination thereof. In one embodiment, all the control systems may be unified via computer interface.

In one embodiment, controlling the environment of the devices will enable multi-hour assays with the cells in their "preferred" environment of, for example, 37° C. with proper pH (~7.2) and oxygen tension. In one embodiment, the devices of this invention may be under controlled physicochemical parameters, which may comprise temperature, pH, oxygen tension, or a combination thereof.

In one embodiment, the devices of this invention may comprise an integrated temperature control system. In one embodiment, on-chip temperature sensing may be conducted, and in another embodiment, may use a microscale calibration technique that gives spatial information.

In one embodiment, the temperature control system may consist of a metal temperature-sensing resistor and a resistively heated transparent conductive heater connected to a computer. The computer implements in software a PID (proportional-integral-differential) controller that in turn controls a heater power supply. The transparent heater may be made, in one embodiment, of indium tin oxide (ITO), a transparent conductor that is commonly used as an electrode in LCD displays and is used as a heater in a commercial environmental chamber for microscopy (Bioptechs, Inc.). In one embodiment, it is possible to place the heater anywhere in the system. In one embodiment, commercially obtained ITO-coated coverslips are used, and the solution is heated directly.

In another embodiment, the performance of the temperature control system can be evaluated using encapsulated thermochromic liquid crystals (TLCs) [Chaudhari, A. M., Woudenberg, T. M., Albin, M. & Goodson, K. E. Transient liquid crystal thermometry of microfabricated PCR vessel arrays. Journal of Microelectromechanical Systems 7, 345-355 (1998)]. These crystals, which are the same active ingredient found in flexible strip thermometers that patients can apply to their foreheads, change color in response to temperature differences and are readily available in formulations with responses centered around physiological temperatures and in particle sizes of several microns, giving adequate spatial resolution. They allow for the spatial integration of the image and the temperature distribution of the chip and through calibration, achieving, in one embodiment, ~0.1° C. accuracy and precision.

In another embodiment, pH is controlled in DMEM-based media via a bicarbonate buffering system. In one embodiment, pH may be measured using a commercial inline microvolume pH sensor. In another embodiment, $O_2$ will be monitored and controlled in the same way as $CO_2$.

In another embodiment, the invention provides a flow chamber comprising the device.

In another embodiment, this invention provides a method of particle patterning comprising the steps of:
a. loading particles on a particle patterning device comprising a first substrate and wells, wherein:
   i. said wells are sized so as to accommodate a requisite number of particles;
   ii. said wells are positioned on or as a part of said substrate; and
   iii. said wells are spaced at defined increments of from about 50 μm to about 50 mm between each well in said device;
b. ensuring said requisite number of particles are within the wells of said device; and
c. positioning said device such that its posterior surface is located apically with respect to a second substrate, its long axis is approximately parallel to the long axis of said second substrate and said second substrate is at a specified distance from said device;
whereby said particles are thereby deposited on said second substrate and patterned according to said defined increments.

In one embodiment, the particles are cells, which in some embodiments, vary in terms of type, dimension, experimental manipulation or combination thereof. In some embodiments, the wells comprise individual cells. In some embodiments, the method further comprises the step of assaying the particle or cell.

The particle patterning devices of the present invention can be used, in some embodiments, to pattern thousands of cells, with single-cell resolution, and concurrently be so constructed so as to allow the cells room to grow.

Figure 2:
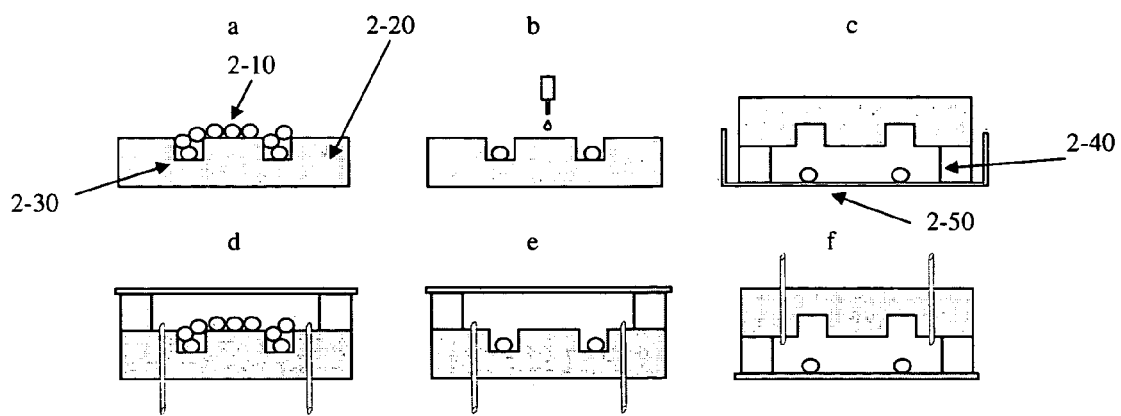
FIG. 2a schematically depicts cells or particles 2-10, applied to a substrate 2-20 with wells 2-30.
FIG. 2b shows application of a wash solution, which facilitates single cell or particle deposition within each well.
FIG. 2c shows the second substrate, 2-50 onto which the substrate is flipped. A spacer 2-40 may be used in the transfer of cells from the first substrate to the second substrate, as described.

The patterning devices of this invention can, in some embodiments, comprise microfabricated polymer chips containing thousands of microwells, each sized to trap down to a single cell level, as demonstrated herein in FIGS. 1 and 2. The device may comprise the chip, or first substrate with wells alone, where the cells or particles are accommodated individually, or per the particular requirements for use. The first substrate or chip, is then flipped over onto a second substrate, which may be a part of the device, in some embodiments, or in other embodiments, may be any desired substrate onto which the deposition of the particles or cells is desired.

In one embodiment, the second substrate, onto which the material is patterned, may be coated, or associated with another material, or another layer of cells. When cells are patterned onto the second substrate, in some embodiments, they can attach after a few hours and proliferate. The patterning device can be a part of an enclosed flow chamber, in some embodiments, (FIGS. 2 d-f), enabling utilization in perfusion culture systems. It is to be understood that the patterning devices of this invention need not be restricted to any specific cell, particle or material, and can be used for anything for which discrete patterning is desired, for example, the device may be used to pattern model cells or other particles as will be described below.

In one embodiment, an advantage to the devices and/or method of the invention is the ability to pattern cells, at a single-cell resolution, concurrent with the ability to pattern them on a surface with much room to proliferate, is not restricted to the type of material of which it is comprised, and the method and device are easy to use, gentle on the material being patterned, an attractive feature, for example, when working with cells or material that is fragile. Other applicable features of the devices and/or methods of the invention are the ability to pattern with high efficiency, pattern thousands of cells on a substrate, and pattern a wide range of designs.

In another embodiment, this invention provides a method of patterned cell analysis comprising the steps of:
 a. loading cells on a cell patterning device comprising a first substrate and wells, wherein:
   said wells are sized so as to accommodate a requisite number of cells;
   said wells are positioned on or as a part of said substrate; and
   said wells are spaced at defined increments of from about 50 μm to about 50 mm between each well in said device;
 b. ensuring said requisite number of cells are within the wells of said device;
 c. positioning said device such that its posterior surface is located apically with respect to a second substrate, its long axis is approximately parallel to the long axis of said second substrate and said second substrate is at a specified distance from said device, whereby said cells are thereby deposited on said second substrate and patterned according to said defined increments; and
 d. analyzing said patterned cells.

In one embodiment, the analyzing is conducted subsequent to cells spreading, proliferation, assay, or a combination thereof. In one embodiment, the assay is a diagnostic assay.

In one embodiment, the cells are engineered to express at least one desired molecule, or in another embodiment, the cells are contacted with a library of molecules prior to loading of the cells. In one embodiment, the cells are assayed to determine efficacy of a molecule within said library, which in one embodiment, is a drug. In one embodiment, the cells are stem or progenitor cells, and in one embodiment, the cells are engineered to express at least one desired protein. In one embodiment, the cells are cultured under conditions promoting expression of the protein, and in one embodiment, the conditions promote tissue engineering as a function of expression.

In one embodiment, the devices and/or methods of the invention modulate cell-cell signaling by patterning single cells in grids of different configurations.

In one embodiment, cells or particles are assayed when positioned on the first or second substrate, or both. In some embodiments, the components of the device are selected such that minimal background contribution of the materials is contributed to the readout of the assy. In some embodiments, such choice in material is a reflection of the reagent used. In one embodiment, the reagent may comprise is an antibody, a nucleic acid, an enzyme, a substrate, a ligand, or a combination thereof, which in turn may be coupled to a detectable marker, which in another embodiment is a fluorescent compound. In one embodiment, according to this aspect of the invention, the substrates may be comprised of a transparent material, and in another embodiment, analysis is carried out using automated microscopy, and may comprise the application of, for example, fluorescence microscopy.

In another embodiment, assay may make use of microscopy, which in turn can be coupled to the devices of the invention, and provide for automated imaging and phenotype acquisition as part of the methods of this invention. In one embodiment, commercially available, automated microscopes by Zeiss, Nikon, etc. which enable the user to control the objectives, fluorescence filters, x-y stage, z-axis (autofocus), diaphragms, etc may be used. According to this aspect, appropriate control software (e.g., Metamorph) may be used, in another embodiment, to set up a timelapse protocol repeatedly taking brightfield and fluorescence pictures of an arbitrary set of fields at arbitrary time intervals.

In one embodiment, the use of two-photon microscopy will be used in order to give greater fluorescence sensitivity, or, in another embodiment, quantum dots may be used for high-brightness live-cell labeling.

In one embodiment, a combination of general assays to test overall long-term effects of cellular manipulations in the patterning methods of this invention may be conducted, which may comprise molecular analysis of the stress response using, for example, immunofluorescence or RT-PCR. In one embodiment, stress responses may be determined via the characterization of changes in both nuclear accumulation and mRNA levels in response to manipulation on-chip.

In one embodiment, stress responses may be determined with the use of model cells, for example, NIH 3T3 fibroblasts grown in standard medium and introduced to the wells of the first substrate, e.g. a microchip, as depicted in FIG. 1. Cells are then flipped onto a second substrate, for example a 24 well plate, and stress responses of the cells are evaluated in the plate. To assess nuclear translocation of hsc70, one may then fix cells with 3.7% formaldehyde, permeabilize them and perform indirect immunofluorescence in situ with an anti-hsc70 monoclonal antibody (e.g., SPA-815 from Stressgen154) and an appropriate secondary antibody. As positive controls for nuclear translocation one can use NIH 3T3 cells grown on 24 well plates under the same conditions that have been exposed to heat shock of 45° C. for 60 min in a water bath, conditions that have been shown to give significant nuclear translocation in HeLa cells and is more than adequate to give hsc70 upregulation in NIH3T3 cells. As negative controls one may use cells seeded on the 24 well plates, which have not been patterned on the plates from another substrate. Software may be used to colocalize hsc70 fluorescence with a nuclear stain such as Hoechst or DAPI using routines such as those used for the Cellomics platform.

In another embodiment, the stress response may be determined via RT-PCR assay of hsc70 and hsp70 mRNA levels, both of which have been shown to be upregulated (as assayed by Northern blot) in NIH 3T3 cells in response to heat shock, for example. NIH 3T3 fibroblasts grown and patterned as described are then flash frozen and stored at −80° C., thawed and total RNA is isolated, for example with a commercial kit optimized for small cell numbers (e.g., Qiagen's RNAEasy micro). RT-PCR with appropriately chosen exon-spanning primers for hsc70 and hsp70 (as well as internal control such as b-actin) is performed. Samples from control cells as described above may be similarly probed.

In one embodiment, the devices and/or methods of this invention find application in various screens. In one embodiment, the screen may be a genetic screen, which in one embodiment has three fundamental steps: 1) alteration of the genetic program of the cell, 2) patterning the altered cell under desired conditions and 3) observation and/or identification of altered phenyotype in the cell as a consequence of the genetic changes. In some embodiments, the method will enable the determination of the elements responsible for the displayed phenotypes. In one embodiment, alteration can be accomplished using the natural (background) mutation rate, or, in another embodiment, inducing mutations with chemicals or UV light, or in another embodiment, introducing exogenous pieces of DNA (e.g., transfection), or, in another embodiment, using small molecules or siRNAs to alter protein function or, in another embodiment, protein expression. In one embodiment, specific patterning of the altered cells, with the ability to control the cellular microenvironment and its downstream effects will dramatically enhance the reach of genetic screens.

In another embodiment, the methods and/or devices enable the determination of behaviors that vary over space and over time. Cells are inherently dynamical systems with specialized compartments. Timescales for relevant phenomena vary over many orders of magnitude, from the subsecond responses of cells to calcium, to the 10's of seconds for ligand-induced protein translocation, to the hours needed for mammalian cells to go through the cell cycle, and each of these timescales may be observed via the methods and/or devices of this invention.

In one embodiment, the methods and/or devices of this invention will use particles and/or cells with fluorescent outputs, such as green fluorescent protein (GFP) or its variants [Tsien, R. Y. The green fluorescent protein. Annual Review of Biochemistry 67, 509-544 (1998)], that indicate, or report, the presence of the phenotype of interest [Taylor, D. L., Woo, E. S. & Giuliano, K. A. Real-time molecular and cellular analysis: the new frontier of drug discovery. Current Opinion in Biotechnology 12, 75-81 (2001); Rutter, G. A., Kennedy, H. J., Wood, C. D., White, M. R. H. & Tavare, J. M. Real-time imaging of gene expression in single living cells. Chemistry & Biology 5, R285-R290 (1998)]. In one embodiment, subcellular localization may be assessed [Rolls, M. M. et al. A visual screen of a GFP-fusion library identifies a new type of nuclear envelope membrane protein. J Cell Biol 146, 29-44. (1999); Peelle, B. et al. Intracellular protein scaffold-mediated display of random peptide libraries for phenotypic screens in mammalian cells. Chem Biol 8, 521-34. (2001; Fujii, G., Tsuchiya, R., Ezoe, E. & Hirohashi, S. Analysis of nuclear localization signals using a green fluorescent protein-fusion protein library. Exp Cell Res 251, 299-306. (1999)], two-hybrid screens for protein interactions may be conducted [Shioda, T., Andriole, S., Yahata, T. & Isselbacher, K. J. A green fluorescent protein-reporter mammalian two-hybrid system with extrachromosomal maintenance of a prey expression plasmid: application to interaction screening. Proc Natl Acad Sci USA 97, 5220-4. (2000)], and reporters of protein tyrosine kinase activity [Ting, A. Y., Kain, K. H., Klemke, R. L. & Tsien, R. Y. Genetically encoded fluorescent reporters of protein tyrosine kinase activities in living cells. Proc Natl Acad Sci USA 98, 15003-8. (2001)] may be effected via visual inspection of fluorescing cells, as described. Fluorescence may also used to study the intracellular dynamics of the cells patterned via the devices of this invention. In one embodiment, fluorescence resonance energy transfer (FRET), which is a sensitive measure of protein-protein interactions, and has been used to study everything from protein localization to kinase activity [Lippincott-Schwartz, J., Snapp, E. & Kenworthy, A. Studying protein dynamics in living cells. Nat Rev Mol Cell Biol 2, 444-56. (2001); Zhang, J., Campbell, R. E., Ting, A. Y. & Tsien, R. Y. Creating new fluorescent probes for cell biology. Nat Rev Mol Cell Biol 3, 906-18 (2002)] may be employed in the devices and/or methods of this invention, and may make use of the spacing in the patterning of the cells on the substrate. In another embodiment, fluorescence recovery after photobleaching (FRAP), may be used to measure protein mobility by, in one embodiment, photobleaching a cell area and measuring the time needed to restore fluorescence from newly introduced fluorophores. In another embodiment, fluorescence correlation spectroscopy (FCS) may be used to measure protein diffusion and concentration in live cells, giving information on, in another embodiment, protein-protein interactions.

In another embodiment, morphology is another phenotypic indicator used in the methods of this invention. In another embodiment, morphological assessment may be complemented with molecular characterization. In another embodiment, morphology is utilized in characterizing cell function, such as for example, and in another embodiment, the determination of cellular apoptosis, which may be determined morphologically, via the observation changes in cell and nuclear morphology over the time course of the process studied.

In one embodiment of this invention, the patterning devices of this invention are extremely versatile and enable automated large scale patterning and subsequent single cell assay. In one embodiment, the devices of this invention may screen 10,000 cells simultaneously, including for example the ability to simultaneously screen, in another embodiment, for dynamic behavior of the expressed protein.

In another embodiment, one-step library screens, such as, in one embodiment, a cDNA or mutant library, of mammalian cells having undergone transient transfections with such libraries may be performed. In another embodiment, screens involving introduced genetic elements using, in one embodiment, stable transfection or in another embodiment, transient transfection with pooled libraries, may be used. In another embodiment, the devices of this invention can be used to isolate single positive-responding cells for immediate genetic analysis, such as, for example, single-cell PCR.

In another embodiment, synthetic genetic regulatory modules introduced into, for example, *E. coli* may be used to investigate genetic regulation and fundamental cell biology, via the methods of this invention. In one embodiment, combinatorial techniques to generate plasmids randomly encoding differing two-input (the small molecules IPTG and aTc) and one output (a GFP reporter) logic functions, may be used as described [Guet, C. C., Elowitz, M. B., Hsing, W. & Leibler, S. Combinatorial synthesis of genetic networks. Science 296, 1466-70. (2002)]. In one embodiment, similar library-based approaches could be extended to dynamic (or even localization) circuits (such as variations on the original repressilator) where cells are easily isolated after extended dynamic monitoring.

In one embodiment, the incorporation of unique non-grid geometries patterning the cells on the second substrate provide a means to assess spatial effects on cells, for example, following exposure to an agent inciting the initiation of an intracellular cascade. Such effects in terms of controlling or promoting cell-cell signaling can similarly be assessed.

In some embodiments, the devices and/or methods of this invention find application in drug discovery. For example, libraries of compounds can be screened on a single cell level, using the devices of this invention. Downstream effects in the singular patterned cell can be evaluated over a prolonged course of time and parallel determinations in multiple cell types or cells can be determined.

In another embodiment, the devices and/or methods of this invention find application in stem cell engineering, or tissue engineering, as described. Patterned cells, including stem cells, can be genetically altered prior or following their deposition onto the second substrate, and effects on cellular phenotype assessed, by any means known in the art. In other embodiments, cells can be spaced sufficiently so as to enable engineering of tissue on the second substrate. In one embodiment, cells may be patterned onto the second substrate repeatedly, over a course of time. In one embodiment, for example, stem cells are initially patterned, and at a later point in time, more differentiated cells, or cells of alternative lineages may be applied to the second substrate to mimic engineering of tissue in vivo. The application of cells, including cells engineered to express multiple, or different proteins, and their application to temporally regulate a desired process, can be readily accomplished via the devices and/or methods of this invention, and provide numerous processes which may be utilized for a staggering number of biological applications, which will be appreciated by one skilled in the art. Such application may be useful for example, in the development of cell-based biosensors, diagnostic assays, cell signaling research, cell tracking studies, and others.

In another embodiment, the devices of this invention find application in the construction of optical colored displays. According to this aspect of the invention, and in one embodiment, a solution comprising hollow particles e.g. vesicles are individually introduced to wells of the first substrate. The vesicles encapsulate a labeled marker, for example, a red dye molecule. The substrate is flipped over a transparent surface and the solution is dried out causing the vesicles to break and release the red dye onto the surface in positions that follows the spacings in the substrate well array. The substrate is cleaned and filled with vesicles that carry blue dye molecules. The substrate is aligned with one well length shift to its former position with respect to the surface. The process is repeated yielding a square area of blue dye molecules next to the square area of the red dye molecules on the transparent surface. The process can be repeated with additional colors to yield a display exhibiting an array of pixels each contains a set of different colors. Each pixel can be later addressed electronically or optically by attaching an appropriate probe to each pixel area.

In another embodiment, the devices and/or methods of this invention may find application in the detection of cell signaling events. In some embodiments, such signaling events are stimulated by proximity, for example, early signaling events in white blood cells when in proximity to a pathogen may be readily determined using the methods and/or devices of the invention. In one embodiment, the first substrate comprises wells sized such that only individual macrophages can be accommodated within the wells. The macrophages are flipped onto a second substrate. Another substrate sized to accommodate varying numbers of bacterial cells, for example, is then flipped on the same substrate, positioning a desired number of pathogens, and cell signaling in the macrophages is determined as a function of bacterial cell number in proximity to the macrophages. In another embodiment, other signaling events in cells may be determined as a function of environmental conditions, cell density, etc. For example, bacterial cells may be patterned at varying density on the second substrate, and the initiation of quorum sensing may then be determined.

In some embodiments, the methods and/or devices may be used to form multiple patterns of particles/cells. According to this aspect, and in one embodiment, the methods and/or devices may be used to pattern a first cell type or particle onto the substrate, and subsequently pattern an additional cell type and/or particle onto the substrate. In some embodiments, multiple rounds of patterning are envisaged. In some embodiments, the second patterning is atop the first cell or particle patterned, or in another embodiment, the second patterning is shifted over by a discrete length, for example one cell or particle length over, so as to produce, for example, a checkerboard of different cells or cell/particle, or particle/particle arrangements. In some embodiments, variation in multiple patterning steps enables arrangements of specific lines/rows of different particles/cells on a single array. In some embodiments, such patterned arrays with repeat patterning steps may be accomplished utilizing the same first substrate twice, or in some embodiments, using multiple first substrates, patterning cells/particles onto the same second substrate.

In some embodiments, this enables patterning of cells onto substrates comprising cells or particles which have not been patterned. Some applications of this principle may include patterning single bacterial cells onto monolayers of immune cells, for example, where the bacterial cells are for example engineered to express a library, which comprises mutations which affect the pathogenesis of the organism. It is to be understood that any manipulation of the patterning devices and/or methods of this invention may be used when the device is stand-alone, or comprises a part of a flow chamber, as herein described.

In some embodiments, the particles for use with the devices and/or methods of this invention comprise a drug, an antibody, a nucleic acid, or any compound of interest. The compound may serve as a probe for a particular function, or to determine expression, or in other embodiments, to treat a particular condition. In some embodiments, such compound-associated beads, which may be physically attached, or attracted to the beads by non-covalent association, may be patterned onto individual cells, multiple patterned arrangements, monolayers of cells, non-patterned cell groupings, etc. There is no limitation to the application of the compound-associated bead to any substrate, in this invention.

In some embodiments, cells can be patterned onto electrodes, and can in turn find application as biosensors, as is well known in the art, for example, as described in U.S. Application Publication Number 20050095630; U.S. Application Publication Number 20050014201; U.S. Application Publication Number 20040048241, and others, as will be appreciated by one of skill in the art.

In some embodiments, the methods and/or devices may be used to determine the effects of specific geometries on cell growth. For example, the particle patterning device may comprise a second substrate with a non-flat surface. The surface according to this aspect, and in one embodiment, may comprise an array of mechanical barriers for the study of cell growth under restricted geometries. The surface is patterned by photolithography followed by an etching step to yield various barrier shapes on it. The surface barriers are closed or partially opened. In one embodiment, the barriers are so constructed so as to result in cell patterning within the voids enclosed or semi-enclosed by the barriers. Cell growth and other responses are then assayed as a function of time and location within the altered geometry. Barrier heights can be easily modified, and many different barrier topographies can be used on a single substrate, whose effects can be readily assayed using the devices and/or methods of this invention.

In some embodiments, the devices and/or methods of this invention may be used to modify surfaces of a substrate. In one embodiment, the first substrate containing wells may be filled with a solution comprising metal particles which deposit the particles in particular desired regions and concentrations on the substrate. The substrate may then be flipped onto a semiconductor surface forming a metal pattern that follows the well or channel array. This pattern can be of any shape including characters and letters. In one embodiment, such method finds application in printing processes. In one embodiment, such method may find application in the patterning of select areas on a substrate with a metal. In another embodiment, the metal particles on the surface can be further annealed to yield a uniform metal layer pattern on a desired surface. In other embodiments, the metal layer can be further modified by an organic material. Other manipulations of this method are readily apparent to one skilled in the art and may be used for the specific patterning or design of any particulate material on a desired substrate.

In another embodiment, the devices and/or methods of this invention find application in the preparation of patterned curved surfaces, which may be used in optical fiber performance enhancement or applications in plastic electronics. In another embodiment, as described herein, the particle patterning device can be used to pattern curved surfaces. The first substrate comprising an array of wells may be constructed of a flexible polymeric material. The first substrate is initially held flat for loading of the particle solution. Following loading, the flexible substrate may then be wrapped around a curved cylindrical surface, which in turn may be rotated around the cylinder axis, enabling patterning of the particles onto the curved surface. The surface and particles may be chosen such that the particles adhere to the curved surface upon contact. This pattern can be of any shape including, in some embodiments, that of characters and letters. Some embodiments of this aspect of the invention comprise use of such a method for printing purposes, plastic electronics or the patterning of optical fibers for performance enhancement. The metal particles on the surface can be further annealed to yield a uniform metal layer pattern on the surface. The metal layer can be further modified by an organic material, in this aspect, as well.

The following examples represent embodiments of the invention, and are not to be construed as limiting the scope of the invention in any way.

EXAMPLES

Example 1

An Embodiment of a Cell Patterning Device

A microfabricated polymer chip containing thousands of microwells, each sized to trap individual cells was constructed, and is depicted in FIG. 1.

A schematic for patterning the cells is provided in FIGS. 2 (a-f). Cells are pipetted onto the surface of the chip, allowing cells to fall into the microwells (FIG. 2 a). After the cells are trapped in the microwells and the other cells are rinsed away (FIG. 2 b), the chip is flipped upside down onto the desired substrate. This substrate can be any material—such as a glass slide, a cell-culture dish coated with another material, or another layer of cells. The cells then fall out of the microwells onto the substrate, where they attach after a few hours and proliferate (FIG. 2 c). The chip has also been validated in an enclosed flow chamber (FIGS. 2 d-f), enabling utilization in perfusion culture systems.

Example 2

Scalability and Accuracy of the Particle Patterning Device

Figure 3:
FIG. 3 shows the device scalability and accuracy. (3A) massively parallel patterning of mESCs on day 1 after seeding. (3B) Zoomed in view of 4 single cells demonstrating the high patterning accuracy.
Figure 3:
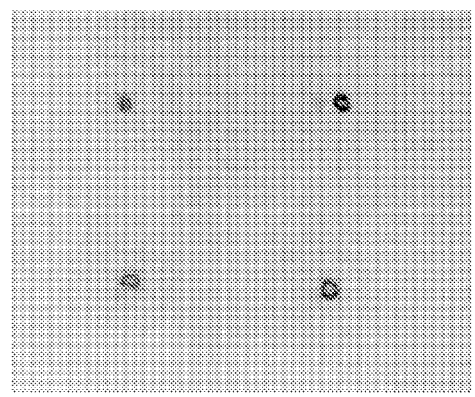

In order to determine scalability of the patterning devices, a 50×50 grid of murine embryonic stem cells were seeded onto a cell-culture dish (FIG. 3A). When multiple patterning runs of murine embryonic stem cells were applied to the device, and flipped onto a cell-culture dish, patterning efficiencies of greater than 75.9% were consistently achieved.

In addition, stem cell patterning showed superior accuracy (FIG. 3B). Using a microwell-microwell spacing of 200±0 μm, cells were patterned onto a cell-culture dish with a cell-cell spacing of 198±17 μm, thus seeding a cell within one cell diameter away from its target location. Cell patterning down to single-cell resolution has been achieved, with 50.0% of the patterned spots resulting in single cells.

Since cell-cell spacing on the grid can be varied using the devices of this invention, the seeding density of patterned cells can also be varied. In addition, the size of each microwell, and thus the number of cells at each patterned spot can be varied.

Example 3

Long-Term Cell Tracking can be Achieved with the Patterning Devices

Figure 4:
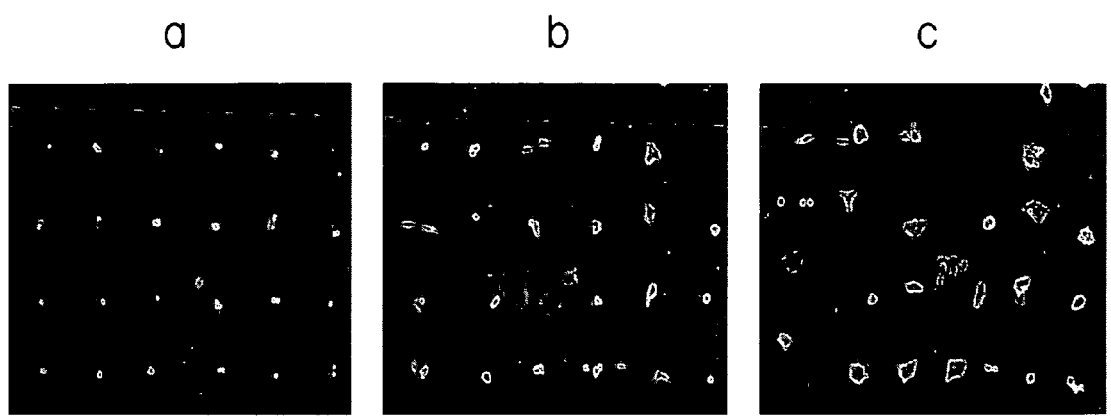
FIG. 4 shows the ability of the device to pattern cells in such a way as to promote long-term cell tracking. Patterned murine embryonic stem cells on (A) day 0, (B) day 1, and (C) day 2 are shown.

Proliferating cells can be patterned with the devices of this invention, and long-term studies a desirable application. Since substrate modification techniques are not necessary for the preparation of the devices of this invention, the cells are not restricted in terms of available area to grow, hence they can proliferate over a long time course, once applied to the second substrate. In addition, because the cells are patterned in a grid, the cell coordinates can be used to track the cells over time, an example of which was validated in FIG. 4. The devices of the invention provide for the ability to monitor changes in cell behavior at the single-cell level, tracking spatial and temporal changes, enabling advantages over populational averaging.

Example 4

Figure 5:
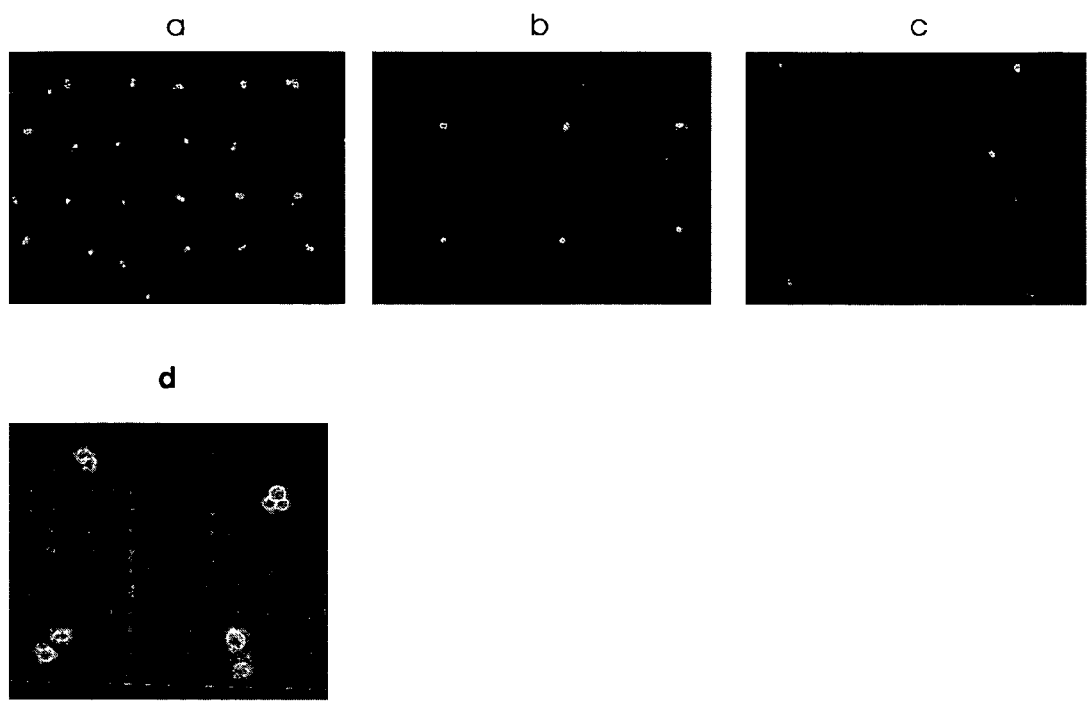
FIG. 5 shows the patterning effects of varying cell-cell spacing, or cell number application. Cells were patterned on the same chip with a cell-cell spacing of: (A) 200 μm, (B) 400 μm, and (C) and 800 μm. (D) shows the results of varying the number of cells patterned at each spot.

Cell Patterning at Different Densities can be Achieved with the Patterning Devices Since the microwells can be fabricated at different densities on the same chip, i.e., spaced apart from each other at different increments, thus cells can be patterned with different cell-cell spacing, once flipped onto the respective substrate. An example of this is provided in FIGS. 5 (a-c), where cells were patterned onto the substrate with a cell-cell spacing of 200 μm, 400 μm, and 800 μm.

Sizing the microwell to be significantly larger than that of an applied cell, allows for the patterning of more than a single cell at respective regions on the substrate (FIG. 5d). Sizing of the microwells can also be such so as to include wells of different size on the same chip and thereby trap different numbers of cells per well on the same chip, for example, or trap cells of different size on the same chip, in another example.

What is claimed is:

1. A method of particle patterning comprising the steps of:
   a. providing a particle patterning device comprising a first substrate, wherein said first substrate contains an array of microwells, and loading particles onto said microwells, wherein:
      i. said wells are sized so as to accommodate a requisite number of said loaded particles;
      ii. said wells are positioned on or as a part of said substrate; and
      iii. said wells are spaced at defined increments of from about 50 μm to about 50 mm between each well in said device;
   b. flipping said first substrate upside down onto a second substrate wherein said second substrate is at a specified distance from said device;
   whereby said particles are thereby deposited from said wells on said second substrate and patterned according to said defined increments.

2. The method of claim 1, wherein said particles are cells or beads.

3. The method of claim 1, wherein said particles are cells and said device is held at atmospheric conditions which promote cell adherence to and proliferation on said second substrate.

4. The method of claim 1, wherein said second substrate is a 96-well plate.

5. The method of claim 1, wherein said particles comprise a compound, a molecule or a macromolecule attached thereto.

6. The method of claim 5, wherein said compound, molecule or macromolecule is a drug, and antibody, a nucleic acid, a peptide, a protein, or a chemical or nucleic acid library.

7. A method of patterning cells comprising the steps of:
   a. providing a particle patterning device comprising a first substrate, wherein said first substrate contains an array of microwells, and loading cells onto said microwells, wherein:
      i. said wells are sized so as to accommodate a requisite number of said loaded cells;
      ii. said wells are positioned on or as a part of said substrate; and
      iii. said wells are spaced at defined increments of from about 50 μm to about 50 mm between each well in said device;
   b. flipping said first substrate upside down onto a second substrate wherein said second substrate is at a specified distance from said device, whereby said cells are thereby deposited from said wells on said second substrate and patterned according to said defined increments; and
   c. analyzing said patterned cells.

8. The method of claim 7, wherein said analyzing is conducted subsequent to cells spreading, proliferation, or a combination thereof.

9. The method of claim 7, wherein said cells are engineered to express at least one desired molecule.

10. The method of claim 7, wherein said cells are contacted with a library of drug molecules prior to said loading of said cells.

11. The method of claim 10, wherein said cells are analyzed to determine the efficacy of said drug molecules in said patterned cells.

12. The method of claim 7, wherein said cells are stem or progenitor cells.

13. The method of claim 12, wherein said cells are engineered to express at least one desired protein.

14. The method of claim 13, wherein said cells are cultured under conditions promoting expression of said protein.

15. The method of claim 14, wherein said conditions that promote tissue engineering as a function of said expression.

16. The method of claim 7, wherein said wells comprise individual cells.

17. The method of claim 7, wherein said device is held at atmospheric conditions which promote cell adherence to and proliferation on said second substrate.

18. The method of claim 7, wherein said second substrate is a 96-well plate.

19. The method of claim 7, wherein said cells are engineered to express a desired nucleic acid molecule.

20. The method of claim 19, wherein said cells express a nucleic acid library.

21. The method of claim 20, further comprising the step of assaying said cells.

22. The method of claim 7, wherein said analyzing comprises tracking spatial and temporal changes at the single-cell level.

23. The method of claim 7, wherein said analyzing comprises detection of cell signalling in the patterned cells.

24. The method of claim 1, wherein said second substrate is a 384-well plate.

25. The method of claim 7, wherein said second substrate is a 384-well plate.

* * * * *